United States Patent [19]

Chen et al.

[11] Patent Number: 5,317,039

[45] Date of Patent: May 31, 1994

[54] CYCLOPROPYL-ALANINE ARYL/ALKYLSULFIDE/SULFONYL-TERMINATED AMINO-DIOL COMPOUNDS FOR TREATMENT OF HYPERTENSION

[75] Inventors: Barbara B. Chen, Glenview; Gunnar J. Hanson, Skokie; John S. Baran, Winnetka, all of Ill.

[73] Assignee: G. D. Searle & Co., Chicago, Ill.

[21] Appl. No.: 916,458

[22] Filed: Jul. 20, 1992

[51] Int. Cl.$^5$ ............................................. A61K 31/16
[52] U.S. Cl. ..................................... 514/616; 564/154
[58] Field of Search ............ 564/154, 155, 157, 158, 564/159; 514/616

[56] References Cited

U.S. PATENT DOCUMENTS

| | | | |
|---|---|---|---|
| 4,619,944 | 10/1986 | Youssefyeh et al. | 514/513 |
| 4,902,706 | 2/1990 | Hanson et al. | 514/400 |
| 4,914,129 | 4/1990 | Bühlmayer et al. | 514/616 |
| 5,032,577 | 7/1991 | Fung et al. | 514/18 |

FOREIGN PATENT DOCUMENTS

| | | | |
|---|---|---|---|
| 30797/89 | 9/1989 | Australia | A61K 37/00 |
| 128762 | 12/1984 | European Pat. Off. | C07C 103/52 |
| 181110 | 5/1986 | European Pat. Off. | C07K 5/06 |
| 186977 | 7/1986 | European Pat. Off. | C07C 103/76 |
| 189203 | 7/1986 | European Pat. Off. | C07K 5/00 |
| 200406 | 12/1986 | European Pat. Off. | C07D 233/64 |
| 216539 | 4/1987 | European Pat. Off. | C07D 295/18 |
| 229667 | 7/1987 | European Pat. Off. | C07K 5/06 |
| 300189 | 1/1989 | European Pat. Off. | C07D 233/64 |
| 0353211 | 1/1990 | European Pat. Off. | . |
| 416373 | 3/1991 | European Pat. Off. | C07D 233/64 |
| 87/04349 | 7/1987 | PCT Int'l Appl. | A61K 37/43 |

OTHER PUBLICATIONS

Umezawa et al, in *J. Antibiot.* (Tokyo), 23, 259-262 (1970).
Gross et al, *Science,* 175, 656 (1971).
Boger et al, *Nature,* 303, 81 (1983).
Kokubu et al, *Biochm. Biophys. Res. Commun.,* 118, 929 (1984).
Castro et al, *FEBS Lett.,* 167, 273 (1984).
Hanson et al, *Biochm. Biophys. Res. Comm.,* 132, 155-161 (1985); 146, 959-963 (1987).

*Primary Examiner*—Richard L. Raymond
*Assistant Examiner*—Brian M. Burn
*Attorney, Agent, or Firm*—J. Timothy Keane

[57] ABSTRACT

Compounds characterized generally as cyclopropyl alanine aryl/alkylsulfide/sulfonyl-terminated amino diol derivatives are useful as renin inhibitors for the treatment of hypertension. Compounds of particular interest are those of the formula

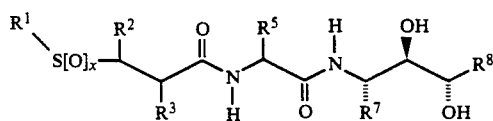

wherein $R^1$ is selected from isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronapthylmethyl and chloronaphthylmethyl; wherein x is zero or two; wherein $R^2$ is selected from hydrido, methyl, ethyl and phenyl; wherein $R^3$ is selected from hydrido, cyclohexylmethyl, benzyl, fluorobenzyl, chlorobenzyl, fluoronaphthylmethyl and chloronaphthylmethyl; wherein $R^5$ is cyclopropylmethyl wherein $R^7$ is cyclohexylmethyl; and wherein $R^8$ is selected from n-propyl, isobutyl, cyclopropyl, cyclopropylmethyl, allyl and vinyl.

25 Claims, No Drawings

CYCLOPROPYL-ALANINE ARYL/ALKYLSULFIDE/SULFONYL-TERMINATED AMINO-DIOL COMPOUNDS FOR TREATMENT OF HYPERTENSION

FIELD OF THE INVENTION

Renin-inhibiting compounds are known for control of hypertension. Of particular interest herein are compounds useful as renin inhibiting agents.

BACKGROUND OF THE INVENTION

Renin is a proteolytic enzyme produced and secreted into the bloodstream by the juxtaglomerular cells of the kidney. In the bloodstream, renin cleaves a peptide bond in the serum protein angiotensinogen to produce a decapeptide known as angiotensin I. A second enzyme known as angiotensin converting enzyme, cleaves angiotensin I to produce the octapeptide known as angiotensin II. Angiotensin II is a potent pressor agent responsible for vasoconstriction and elevation of cardiovascular pressure. Attempts have been made to control hypertension by blocking the action of renin or by blocking the formation of angiotensin II in the body with inhibitors of angiotensin I converting enzyme.

Classes of compounds published as inhibitors of the action of renin on angiotensinogen include renin antibodies, pepstatin and its analogs, phospholipids, angiotensinogen analogs, pro-renin related analogs and peptide aldehydes.

A peptide isolated from actinomyces has been reported as an inhibitor of aspartyl proteases such as pepsin, cathepsin D and renin [Umezawa et al, in *J. Antibiot. (Tokyo)*, 23, 259–262 (1970)]. This peptide, known as pepstatin, was found to reduce blood pressure in vivo after the injection of hog renin into nephrectomized rats [Gross et al, *Science*, 175, 656 (1971)]. Pepstatin has the disadvantages of low solubility and of inhibiting acid proteases in addition to renin. Modified pepstatins have been synthesized in an attempt to increase the specificity for human renin over other physiologically important enzymes. While some degree of specificity has been achieved, this approach has led to rather high molecular weight hepta- and octapeptides [Boger et al, *Nature*, 303, 81 (1983)]. High molecular weight peptides are generally considered undesirable as drugs because gastrointestinal absorption is impaired and plasma stability is compromised.

Short peptide aldehydes have been reported as renin inhibitors [Kokubu et al, *Biochim, Biophys. Res. Commun.*, 118, 929 (1984); Castro et al, *FEBS Lett.*, 167, 273 (1984)]. Such compounds have a reactive C-terminal aldehyde group and would likely be unstable in vivo.

Other peptidyl compounds have been described as renin inhibitors. EP Appl. #128,762, published Dec. 18, 1984, describes dipeptide and tripeptide glyco-containing compounds as renin inhibitors [also see Hanson et al, *Biochm. Biophys. Res. Comm.*, 132, 155–161 (1985), 146, 959–963 (1987)]. EP Appl. #181,110, published May 14, 1986, describes dipeptide histidine derivatives as renin inhibitors. EP Appl. #186,977 published Jul. 9, 1986 describes renin-inhibiting compounds containing an alkynyl moiety, specifically a propargyl glycine moiety, attached to the main chain between the N-terminus and the C-terminus, such as N-[4(S)-[(N)-[bis(1-naphthylmethyl)acetyl]-DL-propargylglycylamino]-3(S)-hydroxy-6-methylheptanoyl]-L-isoleucinol. EP Appl. #189,203, published Jul. 30, 1986, describes peptidyl-aminodiols as renin inhibitors. EP Appl. #200,406, published Dec. 10, 1986, describes alkylnaphthylmethylpropionyl-histidyl aminohydroxy alkanoates as renin inhibitors. EP Appl. #216,539, published Apr. 1, 1987, describes alkylnaphthylmethylpropionyl aminoacyl aminoalkanoate compounds as renin inhibitors orally administered for treatment of renin-associated hypertension. PCT Application No. WO 87/04349, published Jul. 30, 1987, describes aminocarbonyl aminoacyl hydroxyether derivatives having an alkylamino-containing terminal substituent and which are described as having renin-inhibiting activity for use in treating hypertension. EP Appl. #300,189 published Jan. 25, 1989 describes amino acid monohydric derivatives having an alkylamino-alkylamino N-terminus and a β-alanine-histidine or sarcosyl-histidine attached to the main chain between the N-terminus and the C-terminus, which derivatives are mentioned as useful in treating hypertension. U.S. Pat. No. 4,902,706 which issued Feb. 13, 1990 describes a series of histidineamide-containing amino alkylaminocarbonyl-H-terminal aminodiol derivatives for use as renin inhibitors. U.S. Pat. No. 5,032,577 which issued Jul. 16, 1991 describes a series of histidineamide-aminodiol-containing renin inhibitors.

Several classes of sulfonyl-containing amino-diol renin-inhibitors compounds are known. For example, EP #229,667 published Jul. 22, 1987 describes generally alkylsulfonyl histidineamide amino diol C-terminated-alkyl compounds as renin inhibitors. Australian Patent Application #30797/89 published Sep. 7, 1989 describes alkylsulfonyl histineamide amino diol C-terminated-alkyl compounds as renin inhibitors, such as (S)-α-[(S)-α-[(t-butyl-sulphonyl)methyl]hydrocinnamamido]-N-[(1S,2R,3RS)-1-(cyclohexylmethyl)-2,3-dihydroxy-4,4-dimethylpentyl]-imidazole-4-propionamide and (S)-α-[(S)-α-[(t-butylsulphonyl)methyl]hydrocinnamamido]-N-[(1S,2R,3S,4RS)-1-(cyclohexylmethyl)-2,3-dihydroxy-4-methylhexyl]imidazole-4-propionamide. U.S. Pat. No. 4,914,129 issued Apr. 3, 1990 describes sulfone-containing amino-hydroxyvaleryl compounds for use as antihypertensive agents, such as the compounds N-[2(S)-benzyl-3-tert-methylsulfonylpropionyl]-His-Cha-Val-n-butylamide and N-[2(R)-benzyl-3-tert-methylsulfonylpropionyl]-His-Cha-Val-n-butylamide. EP #416,373 published Mar. 13, 1991 describes alkylsulfonyl histidineamide amino diol compounds as renin-inhibitors, such as (S)-α-[(S)-α-[(tert-butylsulfonyl)methyl]-hydrocinnamamido]-N-[(1S,2R,3S)-1-(cyclohexylmethyl)-3-cyclopropyl-2,3-dihydroxypropyl]-imidazol-4-propionamide and (S)-α-[(S)-α-[(tert-butylsulfonyl)methyl]-hydrocinnamamido]-N-[(1S,2R,3R/S)-1-(cyclohexylmethyl)-3-cyclopropyl-2,3-dihydroxybutyl]imidazol-4-propionamide.

DESCRIPTION OF THE INVENTION

Cycloalkylalkyl alanine aryl/alkylsulfonyl-terminated amino diol compounds, having utility as renin inhibitors for treatment of hypertension in a subject, constitute a family of compounds of general Formula I:

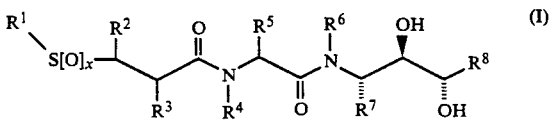

wherein $R^1$ is a group selected from alkyl, trifluoromethyl, cycloalkyl, cycloalkylalkyl, aryl, haloaryl, aralkyl and haloaralkyl; wherein x is a number selected from zero, one and two; wherein $R^2$ is selected from hydrido and alkyl; wherein $R^3$ is a group selected from hydrido, cycloalkylalkyl, aralkyl and haloaralkyl; wherein each of $R^4$ and $R^6$ is a group independently selected from hydrido and methyl; wherein $R^5$ is selected from cycloalkylalkyl groups containing from three to about twelve carbon atoms; wherein $R^7$ is a group selected from alkyl, cycloalkylalkyl and aralkyl; wherein $R^8$ is a group selected from hydrido, alkyl, hydroxyalkyl, cycloalkyl, cycloalkylalkyl, alkenyl and haloalkenyl; and wherein any one of said $R^1$ through $R^8$ groups having a substitutable position may be substituted with one or more groups selected from alkyl, hydroxy, alkoxy and alkenyl.

A preferred family of compounds consists of compounds of Formula I wherein $R^1$ is selected from alkyl, trifluoromethyl, cycloalkyl, cycloalkylalkyl, phenyl, halophenyl, phenylalkyl, halophenylalkyl, naphthyl, halonaphthyl, naphthylaklyl and halonaphthylalkyl; wherein x is a number selected from zero, one and two; wherein $R^2$ is selected from hydrido and alkyl; wherein $R^3$ is selected from hydrido, cycloalkylalkyl, phenylalkyl, halophenylalkyl, naphthylalkyl and halonaphthylalkyl; wherein each of $R^4$ and $R^6$ is independently selected from hydrido and methyl; wherein $R^5$ is selected from cyclopropylmethyl, cyclopropylethyl, cyclobutylmethyl, cyclobutylethyl, cyclopentylmethyl, cyclopentylethyl, cyclohexylmethyl, cyclohexylethyl, cycloheptylmethyl and cycloheptylethyl; wherein $R^7$ is selected from cyclohexylmethyl and benzyl, either one of which may be substituted with one or more groups selected from alkyl, hydroxy and alkoxy; and wherein $R^8$ is selected from hydrido, alkyl, cycloalkyl, cycloalkylalkyl, hydroxyalkyl, alkenyl and haloalkenyl.

A more preferred family of compounds consists of compounds of Formula I wherein $R^1$ is selected from methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from zero, one and two; wherein $R^2$ is selected from hydrido, methyl, ethyl and n-propyl; wherein $R^3$ is selected from hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from hydrido and methyl; wherein $R^5$ is selected from cyclopropylmethyl, cyclopropylethyl, cyclobutylmethyl, cyclobutylethyl, cyclopentylmethyl, cyclopentylethyl, cyclohexylmethyl and cyclohexylethyl; wherein $R^7$ is cyclohexylmethyl; and wherein $R^8$ is selected from methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

An even more preferred family of compounds consists of compounds Formula I wherein $R^1$ is selected from methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein $R^2$ is selected from hydrido, methyl, ethyl and n-propyl; wherein $R^3$ is selected from hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein $R^5$ is selected from cyclopropylmethyl, cyclopropylethyl, cyclobutylmethyl, cyclobutylethyl, cyclopentylmethyl, cyclopentylethyl, cyclohexylmethyl, cyclohexylethyl and cyclohexylpropyl; wherein $R^7$ is cyclohexylmethyl; and wherein $R^8$ is selected from ethyl, n-propyl, n-butyl, isobutyl, cyclopropyl, cyclobutyl, cyclopropylmethyl, allyl and vinyl.

A highly preferred family of compounds consists of compounds of Formula I wherein $R^1$ is selected from isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaptthylmethyl and chloronaphthylmethyl; wherein x is zero or two; wherein $R^2$ is selected from hydrido, methyl, ethyl and phenyl; wherein $R^3$ is selected from hydrido, cyclohexylmethyl, benzyl, fluorobenzyl, chlorobenzyl, fluoronaphthylmethyl and chloronaphthylmethyl; wherein each of $R^4$ and $R^6$ is hydrido; wherein $R^5$ is selected from cyclopropylmethyl, cyclopropylethyl, cyclopentylmethyl, cyclopentylethyl, cyclohexylmethyl and cyclohexylethyl; wherein $R^7$ is cyclohexylmethyl; and wherein $R^8$ is selected from n-propyl, isobutyl, cyclopropyl, cyclopropylmethyl, allyl and vinyl.

The term "hydrido" denotes a single hydrogen atom (H). This hydrido group may be attached, for example, to an oxygen atom to form a hydroxyl group; or, as another example, one hydrido group may be attached to a carbon atom to form a >CH— group; or, as another example, two hydrido groups may be attached to a carbon atom to form a —CH$_2$— group. Where the term "alkyl" is used, either alone or within other terms such s "hydroxylalkyl", the term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about six carbon atoms. The term "cycloalkyl" embraces cyclic radicals having three to about ten ring carbon atoms, preferably three to about six carbon atoms, such as cyclopropyl, cyclobutyl, cyclopentyl and cyclohexyl. The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably two to about ten carbon atoms, and containing at least one carbon-carbon triple bond. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. Preferred aryl groups are those consisting of one, two, or three benzene rings. The term "aryl" embraces aromatic radicals such as phenyl, naphthyl and biphenyl. The term "aralkyl" embraces aryl-substituted alkyl radicals such as benzyl, diphenylmethyl, triphenylmethyl, phenyl-ethyl, phenylbutyl and diphenylethyl. The terms "benzyl" and "phenylmethyl" are interchangeable. Each of the terms sulfide, sulfinyl, and "sulfonyl", whether used alone or linked to other terms, denotes, respectively, the divalent radicals

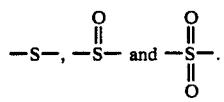

may have a plurality of unsaturated bonds, with such plurality of bonds either adjacent, such as allene-type structures, or in conjugation, or separated by several saturated carbons.

Also included in the family of compounds of Formula I are isomeric forms, including diastereoisomers.

Compounds of Formula I would be useful to inhibit enzymatic conversion of angiotensinogen to angiotensin I. When administered orally, a compound of Formula I would be expected to inhibit plasma renin activity and, consequently, lower blood pressure in a mammalian subject (e.g., a human subject). Thus, compounds of Formula I would be therapeutically useful in methods for treating hypertension by administering to a hypertensive subject a therapeutically-effective amount of a compound of Formula I. The phrase "hypertensive subject" means, in this context, a mammalian subject suffering from or afflicted by the effects of hypertension, or susceptible to a hypertensive condition if not treated to prevent or control such hypertension.

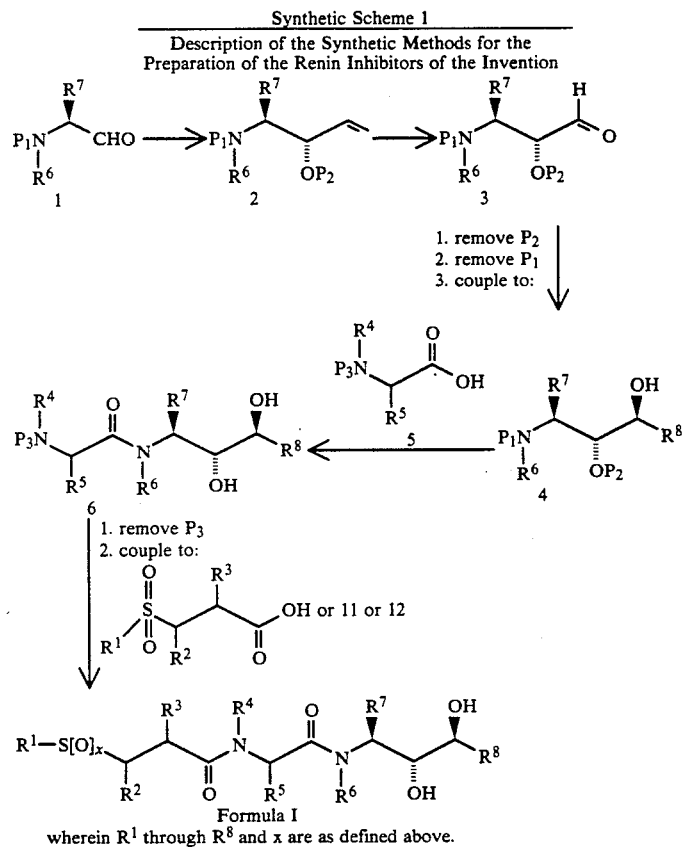

wherein $R^1$ through $R^8$ and x are as defined above.

The term "alkenylalkyl" denotes a radical having a double-bond unsaturation site between two carbons, and which radical may consist of only two carbons or may be further substituted with alkyl groups which may optionally contain additional double-bond unsaturation. For any of the foregoing defined radicals, preferred radicals are those containing from one to about fifteen carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or A suitably protected amino aldehyde 1 is treated with a Grignard reagent or other organometallic reagent, preferably vinylmagnesium bromide, to obtain the vinyl carbinol 2. This material, suitably protected, is oxidized, preferably with ozone, followed by dimethyl sulfide or zinc treatment, to give intermediate 3. The preceeding process is exemplified in Hanson et al, *J. Org. Chem.*, 50, 5399 (1985). This aldehyde is reacted with an organometallic reagent such as isobutylamagnesium chloride to give intermediate 4. Other suitable organometallic reagents include ethylmagnesium bromide, vinylmagnesium bromide, cyclopropylmagnesium bromide, and allylmagnesium bromide, but the choices are not limited to these reagents. After the formation of 4, further transformation of the added side chain is permitted, before going on the next depicted step. For example, the compound 4 derived from the addition of allylmagnesium bromide may be cyclopropanated via diazomethane and rhodium acetate, to give a cyclopropylmethyl side chain. Compound 4 is deprotected then coupled, using standard amide/peptide coupling methodology to protected cycloalkylalkyl-containing amino acid derivatives 5 to give compound 6. These standard coupling procedures such as the carbodiimide, active ester (N-hydroxysuccinimide), and mixed carbonic anhydride methods are shown in Benoiton et al, *J. Org. Chem.*, 48, 2939 (1983) and Bodansky et al, "Peptide Synthesis", Wiley (1976). Cyclopropylemethyl-containing amino acid derivatives may be prepared by cyclopropanation of allylglycine using procedures such as found in Borbruggen, *Tetrahedron Letters*, 9, 629 (1975). Intermediate 6 is then deprotected, then coupled to intermediate 7 or 11 or 12 using the standard amide/peptide coupling methodology, to give compounds of Formula I. Suitable protecting groups may be selected from among those reviewed by R. Geiger in "The Peptides", Academic Press, New York vol. 2 (1979). For example, $P_1$ or $P_3$ may by Boc or Cbz; $P_2$ may be a typical oxygen protective group such as acetyl or t-butyldimethylsilyl.

Synthetic Scheme 2

Preparation of 7:

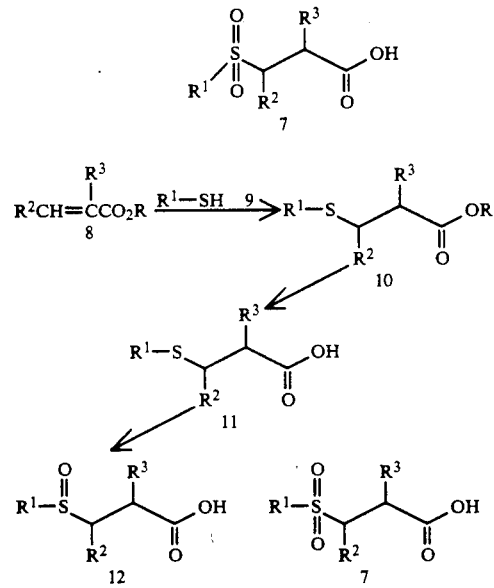

wherein $R^1$, $R^2$ and $R^3$ are as defined above and R is lower alkyl.

Intermediate 7 may be prepared according to Synthetic Scheme 2. Michael addition of a suitable thiol 9 to a suitable acrylic acid 8 in the presence of base catalysts such as sodium hydride, triethyl amine or benzyltrimethylammonium hydroxide, afforded $\alpha,\beta$ di-substituted thio-propionic acid alkyl esters 10. In the case of $R^2=H$, a suitable malonic acid dialkyl ester is hydrolyzed to a mono ester, followed by concomitant decarboxylative dehydration to provide $\alpha$ substituted acrylic acid alkyl ester. Compound 10 is converted into its corresponding sulfone acid 7 via base hydrolysis, followed by oxidation with potassium peroxomonosulfate or perbenzoic acid. Compound 10 may also be converted into its corresponding thio-propionic acid 11 via base hydrolysis. Compound 11 then is further converted into its corresponding sulfoxide acid 12 via 3-chloroperbenzoic acid oxidation.

Abbreviations: $P_1$ is an N-protecting group; $P_2$ is H or an oxygen protecting group; $P_3$ is an N-protecting group.

The following Steps 1–8 constitute specific exemplification of methods to prepare starting materials and intermediates embraced by the foregoing generic synthetic schemes. Those skilled in the art will readily understand that known variations of the conditions and processes of the following preparative procedures can be used to prepare the compounds of Steps 1–8. All temperatures expressed are in degrees Centigrade. Compounds of Examples 1–3 may be prepared by using the procedures described in the following Steps 1–8:

Step 1: Preparation of (2R,3S)-N-[(tert-Butyloxy)carbonyl]-3-amino-2-acetoxy-4-phenylbutanal Ozone/oxygen was bubbled at −70° C. into a solution of (3S,4S)-N-[(tert-Butyloxy)carbonyl]-4-amino-3-acetoxy-5-phenylpentene (2.55 g, 8.0 mmol) [prepared by the method of Hanson, et al., *J. Org. Chem.*, 50, 5399 (1985)] in 100 mL of methylene chloride until a deep blue color persisted. Oxygen was introduced until the blue color completely faded, then 3.0 mL of Me₂S was added and the solution was allowed to warm to 0°–5° C. and stand overnight. The solvent was removed at 0° C. under vacuum yielding the title compound as a thick yellow oil which was used in the following step without purification.

Step 2: Preparation of (2S,3R,4S)-N-[(tert-Butyloxy)carbonyl]-2-amino-1-phenyl-3,4-dihydroxy-6-methylheptane The oil prepared in Step 1 was dissolved under nitrogen in 100 mL of dry THF and cooled to −70° C. To this solution was added 13 mL (26 mmol) of a 2.0M solution of isobutylmagnesium chloride in ether and the stirred mixture was allowed to warm to room temperature and stir for 2 hrs. After decomposition with MeOH/H₂O the mixture was diluted with ether, washed with saturated NH₄Cl solution twice, then dried and the solvents stripped off under vacuum. The residue was allowed to stand overnight in 80% MeOH—H₂O containing excess ammonium hydroxide. The MeOH was stripped off and the mixture was extracted with ether. These extracts were combined, washed with water, dilute KHSO₄, then dried and evaporated to give 2.36 g of a yellow glass which crystallized from 50 mL of pentane on standing overnight. The yellow-white powder obtained was recrystallized from etherhexane and furnished the title compound (0.41 g) as white, hairy needles, mp 134°–136° C., Rf (ether): single spot, 0.6. By chromatography of the mother liquors and crystallization of the appropriate fractions, an additional 0.22 g of product, mp 138°–139° C., was obtained.

Anal: Calcd. for C₁₉H₃₁NO₄ (337.45): C, 67.62; H, 9.26; N, 4.15. Found: C, 67.51; H, 9.43; N, 4.24.

Step 3: Preparation of (2S,3R,4S)-N-[(tert-Butyloxy)carbonyl]-2-amino-1-cyclohexyl-3,4-dihydroxy-6-methylheptane The diol of Step 2, 0.27 g, was reduced in MeOH with 60 psi $H_2$ at 60° C. in 3 hours using 5% Rh/C catalyst. After filtering, the solvent was stripped off and the white crystals were recrystallized from $CH_2Cl_2$-hexane to furnish tiny needles of the title compound, 0.19 g, mp 126°–128° C.; further recrystallization gave mp 128.5°–129.5° C. Rf (ether): single spot, 0.8.

Anal: Calcd. for $C_{19}H_{37}NO_4$ (343.50): C, 66.43; H, 10.86, N, 4.08. Found: C, 66.43; H, 11.01; N, 4.03.

Step 4: Preparation of (2S,3R,4S)-2-amino-1-cyclohexyl-3,4-dihydroxy-6-methylheptane The title compound of Step 3 (10 g) was dissolved 6.9N HCl in dioxane (300 mL). The mixture was stirred for 30 minutes at room temperature. The solvent was removed in vacuo and to the residue was added 5% aqueous sodium hydroxide (30 mL) until a pH of 14 was obtained. This mixture was extracted with ether and the ether extract was washed with water and brine, then the solvent was evaporated to give the title compound (7.3 g, 100% yield).

$^1$H NMR: 300 MHz spectrum consistent with proposed structure.

Anal: calcd. for $C_{14}H_{29}NO_2$: C, 69.07; H, 12.01; N, 5.78. Found: C, 69.19; H, 12.34; N, 5.78.

Step 5: Preparation of N-[1S,1R*-(cyclohexylmethyl)-2S*,3R*-dihydroxy-5-methylhexyl]-2R*-[(1,1-dimethylethoxy)carbonyl]amino]-4-penteneamide 1-methylpiperidine (286 mg, 2.88 mmol) was added to a stirred solution of L-t-Boc-allylglycine (620 mg, 2.88 mmol) in methylene chloride (10 mL). After the reaction flask was cooled to −10° C., isobutyl chloroformate (393 mg, 2.88 mmol) was added, and the reaction was stirred for 5 min at −10° C. whereupon the title compound of Step 4 (700 mg, 2.88 mmol) in 2:1 methylene chloride:tert-butanol (10 ml) was introduced. The solution was allowed to warm to 0° C. over a 30 min period and was maintained at 0° C. for 15 hours. The reaction mixture was evaporated to dryness and then redissolved in ethyl acetate. This was washed successively with 1N citric acid, saturated sodium bicarbonate, water and brine. The solution was dried ($MgSO_4$) and evaporated. The crude product was purified by flash chromatography on silica gel, eluting with 50:25:25 $CH_2Cl_2$:Hex:$Et_2O$ to give pure title compound as white solid (126 mg, 46% yield).

$^1$H NMR: 300 MHz spectrum consistent with proposed structure.

Step 6: Preparation of N-[1S,1R*-(cyclohexylmethyl)-2S*,3R*-dihydroxy-5-methylhexyl]-αR*-[(1,1-dimethylethoxy)carbonyl]aminocyclopropanpropanamide To the title compound of Step 5 (300 mg, 0.68 mmol) and Pd(OAc)$_2$ (2 mg) in ether (3 ml) an ethereal $CH_2N_2$ solution (10 ml, prepared from 412 mg N-nitroso-N-methyl urea) was added dropwise at 0° C. with continuous stirring for 40 min. Glacial acetic acid (1 ml) was introduced to remove excess $CH_2N_2$. The reaction mixture was washed successively with water, saturated sodium bicarbonate and brine. The solution was dried ($MgSO_4$) and evaporated (280 mg, 90% yield).

$^1$H NMR: 300 MHz spectrum consistent with proposed structure.

Anal: calcd. for $C_{25}H_{46}N_2O_5$: C, 66.04; H, 10.20; N, 6.16. Found: C, 65.81; H, 10.26; N, 6.02.

Step 7: Preparation of αR*-amino-N-[1S,1R*-(cyclohexylmethyl)-2S*,3R*-dihydroxy-5-methylhexyl]-cyclopropanpropanamide The title compound of Step 6 (280 mg, 0.67 mmol) was dissolved in methylene chloride (2 ml) and cooled to 0° C. To the reaction mixture trifluoroacetic acid (4 ml) was added quickly and continuous stirring for 1 hr. The reaction mixture was then concentrated and the residue treated with excess aqueous $NaHCO_3$, extracted with ethyl acetate (3×10 ml). The combined organic phase was dried ($Na_2SO_4$) and then concentrated to afford the title compound (120 mg, 55% yield).

$^1$H and $^{13}$C NMR: 300 MHz spectrum consistent with proposed structure.

Anal: calcd. for $C_{20}H_{38}N_2O_3$+0.2 $H_2O$ Calc., C:67.08, H:10.81, N:7.82, Found:C:67.09, H:10.55, N:7.70.

Step 8: Preparation of R,S-2-Benzyl-3-tertbutylsulphonyl-proionic acid

The title compound of Step 8 was prepared by procedures described in Step 8(a) to (d), below:

Step (a): Preparation of α-benzylacrylic acid ethyl ester:

A mixture of 8.5 g of KOH in 100 ml of ethanol was added at room temperature to 40 g of benzylmalonic acid diethyl ester in 80 ml of ethanol. The mixture was stirred overnight at room temperature, then concentrated by evaporation, thereafter 14 ml of water was added and then the mixture was acidified in an ice bath with 12.6 ml of concentrated hydrochloric acid. Partitioning between water and ether was carried out, the organic phase was dried and the ether was distilled off. Then, 26 ml of pyridine, 1.22 g of piperidine and 3.56 g of paraformaldehyde were added to the residue. The mixture was heated in an oil bath (130°) for 90 minutes, cooled, 440 ml of water was added and extraction was carried out 3 times with 150 ml of n-hexane. The combined organic phases were washed alternatively with water, 1N HCl, water, saturated $NaHCO_3$ solution and brine. The solution was dried ($MgSO_4$) and evaporated to give the title compound as colorless oil (26 g, 85% yield)

$^1$H NMR: 300 MHz spectrum consistent with proposed structure.

Step (b): Preparation of 2-benzyl-3-tert.-butylthiopropionic acid ethyl ester:

4.0 g of α-benzylacrylic acid ethyl ester was dissolved in 40 ml of THF and reacted at room temperature with a mixture of 2.39 ml of tert.-butylmercaptan and 459 mg of sodium hydride dispersion (60% in oil). The mixture was stirred at room temperature for 5 hours, poured into 1N hydrochloric acid and extracted with ethyl acetate. The extracts were dried and concentrated by evaporation. The residue was purified by flash chromatography on silica gel, eluting with hexane-ethyl acetate (8:1). Colorless oil (4 g, 68% yield).

$^1$H NMR: 300 MHz spectrum consistent with proposed structure.

Anal: calcd. for $C_{16}H_{24}O_2S$: C, 68.53; H, 8.63. Found: C, 68.10; H, 8.47.

Step (c): Preparation of 2-benzyl-3-tert.-butylthio-propionic acid:

400 mg of 2-benzyl-3-tert.-butylthio-propionic acid ethyl ester was dissolved in 1.5 ml of methanol and then reacted with 5 ml of 2N potassium hydroxide solution. The mixture was stirred overnight at room temperature and concentrated by evaporation. The residue was diluted with water and washed with ether. The aqueous layer was acidified to pH 3 with 2N HCl, and then evaporated to give the title compound (280 mg, 78% yield).

$^1$H NMR: 300 MHz spectrum consistent with proposed structure.

Step (d): Preparation of 2-benzyl-3-tert.-butylsulphonylpropionic acid:

280 mg of 2-benzyl-3-tert.-butylthio-propionic acid was dissolved in 5 ml of methanol and, while cooling with ice, 1 g of potassium peroxomonosulfate in 4 ml of water was added and the whole was stirred overnight at room temperature. The solution was diluted with water and extracted with methylene chloride, and the extracts were dried and concentrated by evaporation (260 mg, 82% yield).

$^1$H NMR: 300 MHz spectrum consistent with proposed structure. Anal: calcd. for $C_{14}H_{20}O_4S$: C, 59.13; H, 7.09. Found: C, 59.39; H, 7.08.

The following working Examples are provided to illustrate synthesis of Compounds 1-36 of the present invention and are not intended to limit the scope thereof. Those skilled in the art will readily understand that known variations of the conditions and processes of the following preparative procedures can be used to prepare the compounds of the Examples. All temperatures expressed are in degrees Centigrade.

EXAMPLE 1

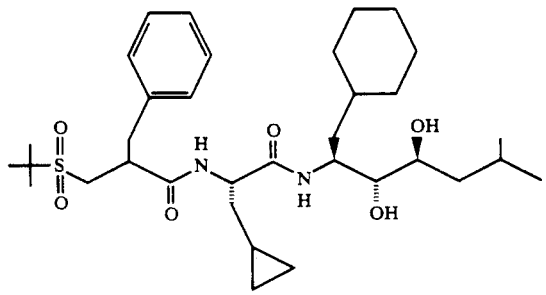

N-[2-[[1S,1R*-(cyclohexylmethyl)-2S*,3R*-
dihydroxy-5-methylhexyl]amino]-1R*-
(cyclopropylmethyl)-2-oxoethyl]-α-[[(1,1-
dimethylethyl)sulfonyl]methyl]benzenepropanamide The acid of Step 8 (143 mg, 0.50 mmol) was dissolved at room temperature in a mixture of dimethylformamide (2 mL) and pyridine (0.2 mL) and to this solution was added N,N'-disuccinimidyl carbonate (119 mg, 0.46 mmol) and 4-dimethylaminopyridine (5 mg). The mixture was stirred for 3 hours, and then the title amine of Step 7 (150 mg, 0.42 mmol) was added, followed by diisopropyl ethylamine (80 µL). This mixture was allowed to stir for 16 hours. The solvent was then evaporated and the residue dissolved in ethyl acetate (15 mL). The mixture was washed successively with water, 0.5M citric acid saturated sodium bicarbonate and brine, then dried over sodium sulfate and the solvent evaporated. The residue was purified by flash chromatography on silica gel, eluting with methylene chloride:methanol (20:1) to give the title compound as a white powder (50 mg, 19% yield).

$^1$H NMR: 300 MHz spectrum consistent with proposed structure.

Anal: calcd. for $C_{34}H_{56}N_2O_6S$: C, 65.77; H, 9.09; N, 4.51. Found: C, 65.59; H, 9.03; N, 4.54.

EXAMPLE 2

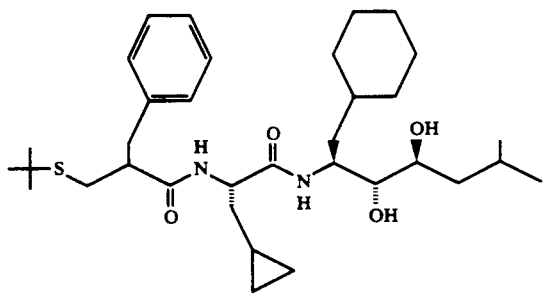

N-[2-[[1S,1R*-(cyclohexylmethyl)-2S*,3R*-
dihydroxy-5-methylhexyl]amino]-1R*-
(cyclopropylmethyl)-2-oxoethyl]-α-[[(1,1-
dimethylethyl)thio]methyl]benzenepropanamide The acid of Step 8 (C) (137 mg, 0.54 mmol) was dissolved at room temperature in a mixture of dimethylformamide (3 mL) and pyridine (0.6 mL) and to this solution was added N,N'-disuccinimidyl carbonate (127 mg, 0.5 mmol) and 4-dimethylaminopyridine (6 mg). The mixture was stirred for 3 hours, and then the title amine of Step 7 (160 mg, 0.45 mmol) was added, followed by diisopropyl ethylamine (87 µL). This mixture was allowed to stir for 16 hours. The solvent was then evaporated and the residue dissolved in ethyl acetate (15 mL). The mixture was washed successively with water, 0.5M citric acid, saturated sodium bicarbonate and brine, then dried over sodium sulfate and the solvent evaporated to give the title compound as a white powder (220 mg, 83% yield).

$^1$H NMR: 300 MHz spectrum consistent with proposed structure.

Anal: calcd. for $C_{34}H_{56}N_2O_4S + 0.7 H_2O$: C, 67.89; H, 9.62; N, 4.66. Found: C, 67.71; H, 9.64; N, 4.73.

EXAMPLE 3

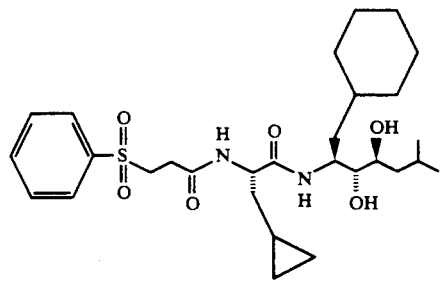

N-[[1S,1R*-(cyclohexylmethyl)-2S*,3R*-
dihydroxy-5-methylhexyl]-αR*-[[1-oxo-3-
(phenylsulfonyl)propyl]amino]cyclopropanepropanamide 3-(Phenylsulfonyl)propionic acid (107 mg, 0.5 mmol) is dissolved in benzene (6 ml) at room temperature. To this, oxalyl chloride (63 mg, 0.5 mmol) and catalytic amount of dimethylformamide are added, and the mixture is allowed to stir for 2 hours. The solvent is then evaporated, and the residue is dissolved in methylene chloride (12 ml) and the title amine of Step 7 (177 mg, 0.5 mmol) is added, followed by 1-methylpiperidine (50 mg, 0.5 mmol). This mixture is allowed to stir for 16 hours. The solvent is then evaporated and the residue is dissolved in ethyl acetate (30 ml), and washed with water, 1N HCl, saturated sodium bicarbonate and brine, then dried ($Na_2SO_4$) and evaporated to give the title compound.

Compounds #4–36, as shown in Table I below, may be synthesized by reference to the foregoing specific and general procedures for preparing compounds of Formula I.

TABLE I

| Example Compound No. | Structure |
| --- | --- |
| 4 | 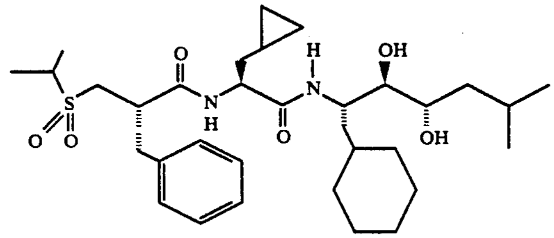 |
| 5 | 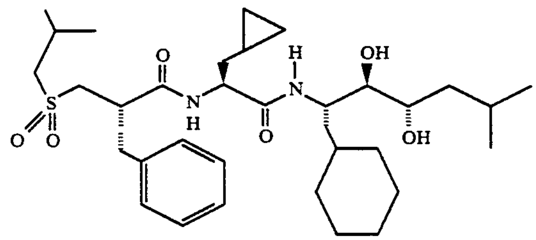 |
| 6 | 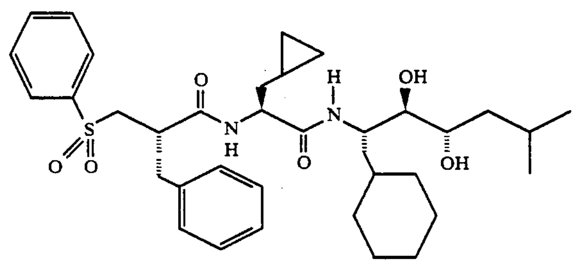 |
| 7 | 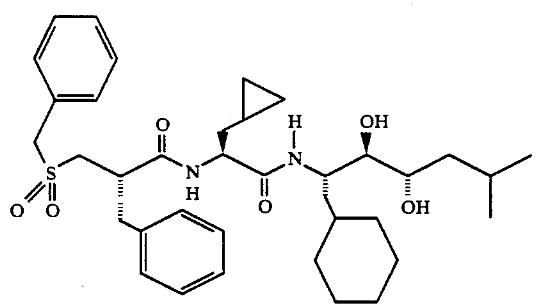 |
| 8 | 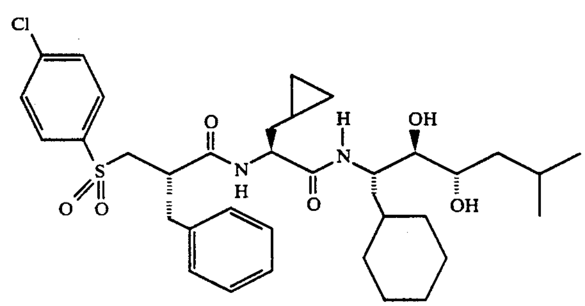 |

TABLE I-continued
| Example Compound No. | Structure |
|---|---|
| 9 | 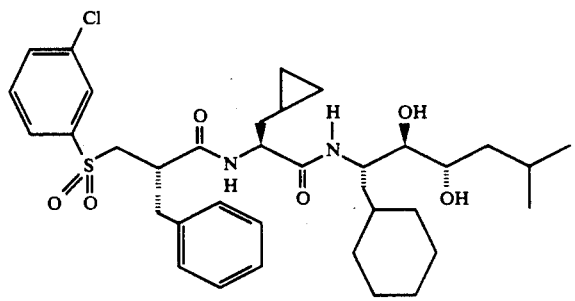 |
| 10 | 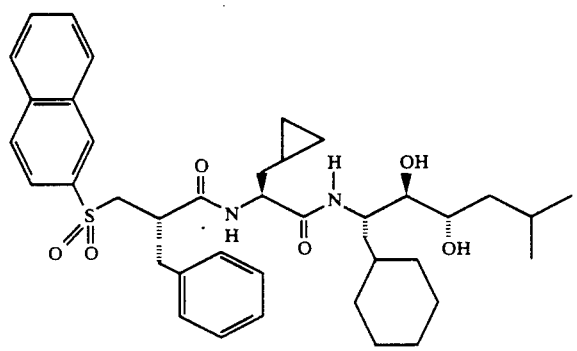 |
| 11 | 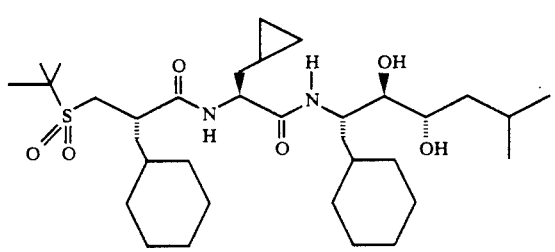 |
| 12 | 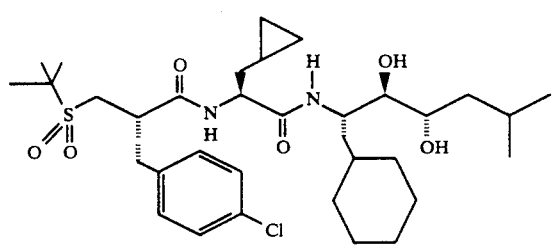 |
| 13 | 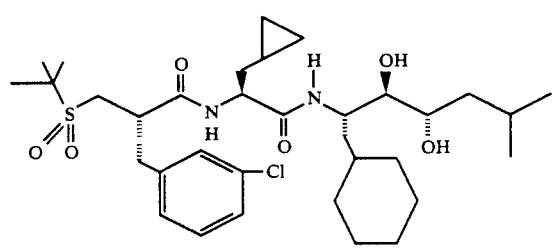 |

TABLE I-continued

| Example Compound No. | Structure |
| --- | --- |
| 14 | 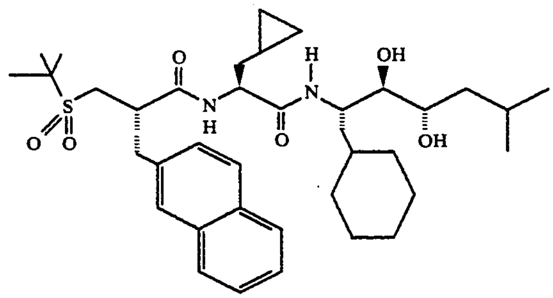 |
| 15 | 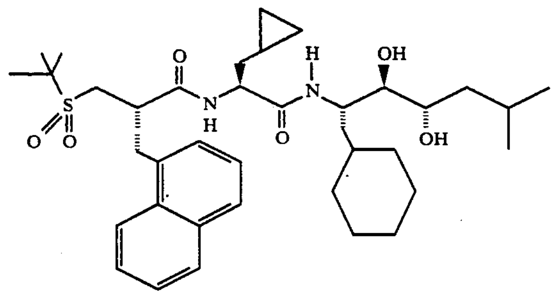 |
| 16 | 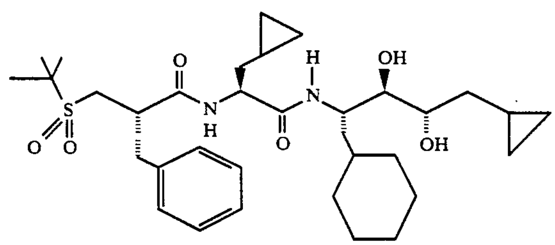 |
| 17 | 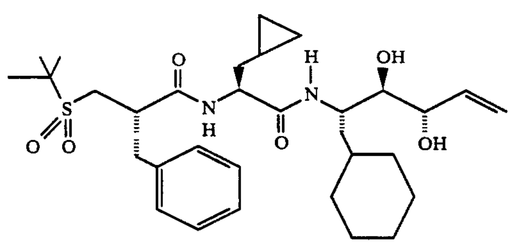 |
| 18 | 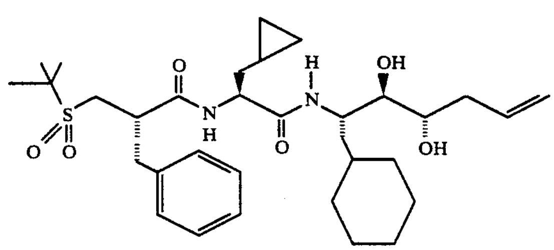 |

TABLE I-continued
| Example Compound No. | Structure |
|---|---|
| 19 | 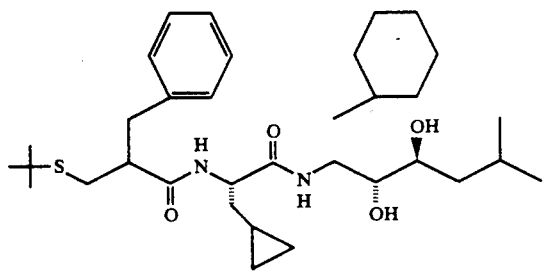 |
| 20 | 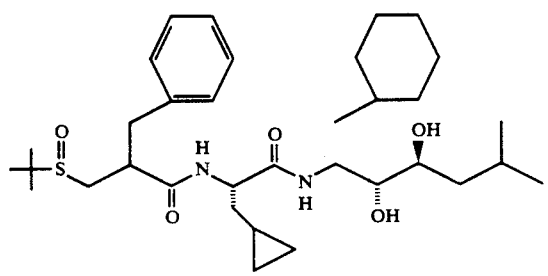 |
| 21 | 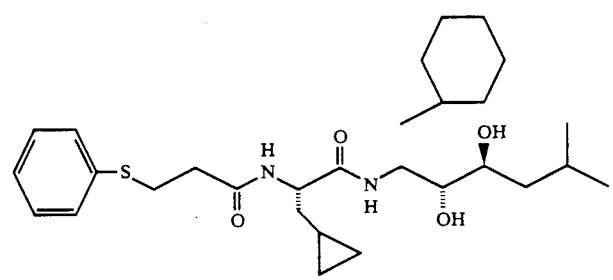 |
| 22 | 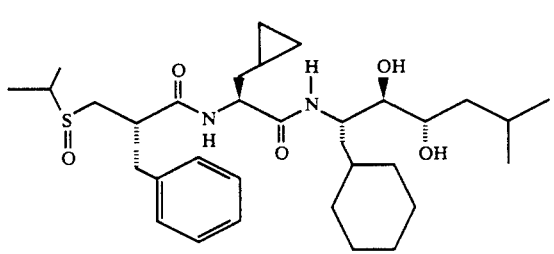 |
| 23 | 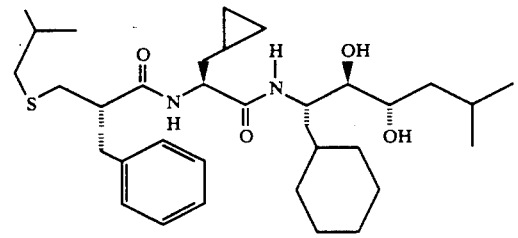 |
| 24 | 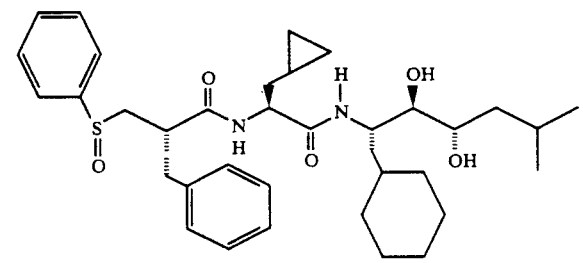 |

TABLE I-continued

| Example Compound No. | Structure |
| --- | --- |
| 25 | 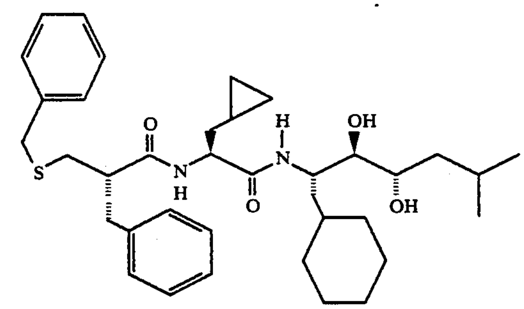 |
| 26 | 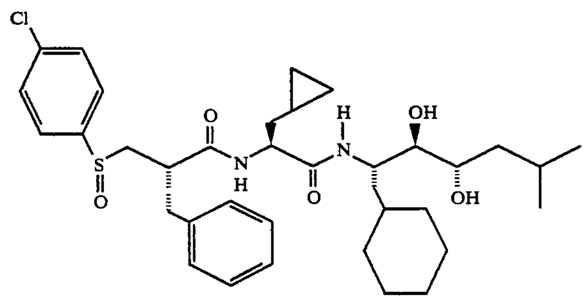 |
| 27 | 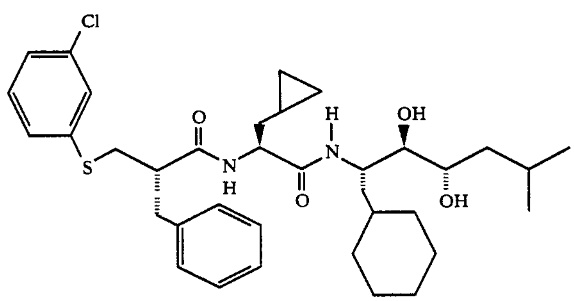 |
| 28 | 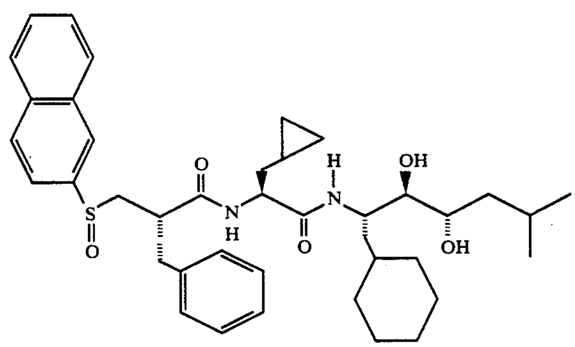 |
| 29 | 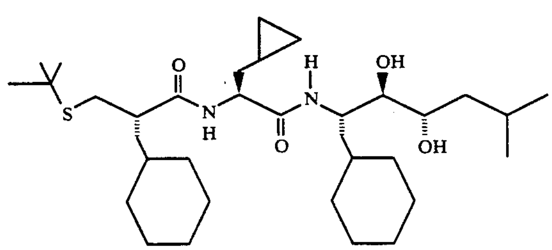 |

TABLE I-continued

| Example Compound No. | Structure |
| --- | --- |
| 30 | 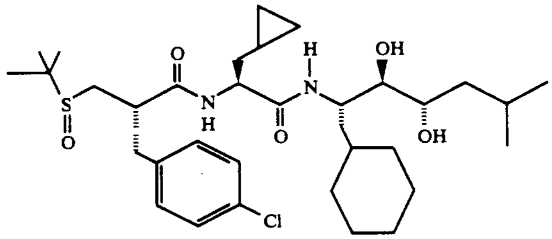 |
| 31 | 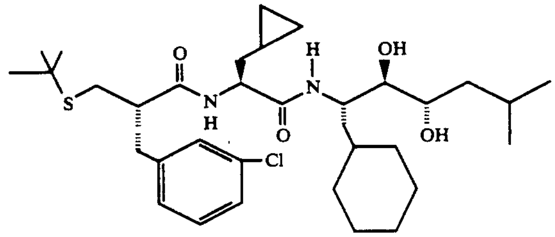 |
| 32 | 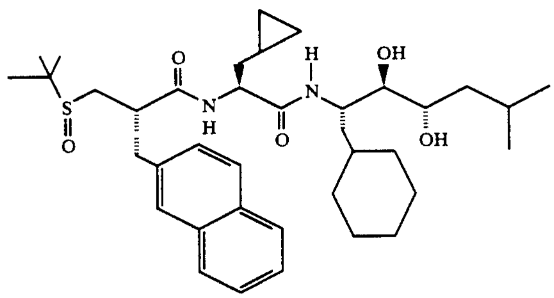 |
| 33 | 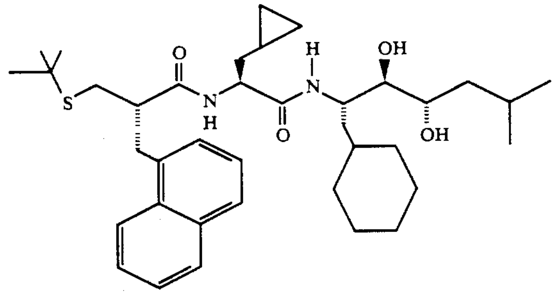 |
| 34 | 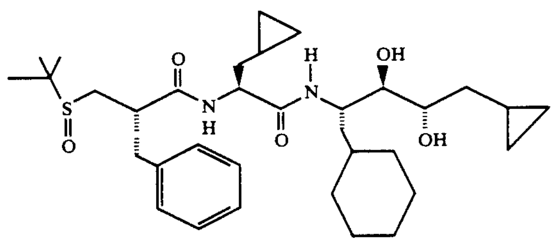 |
| 35 | 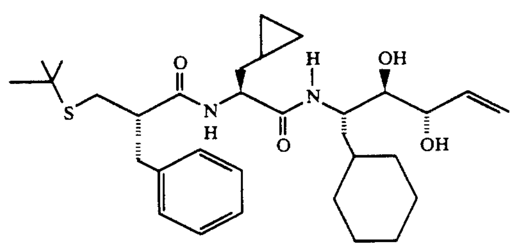 |

TABLE I-continued

| Example Compound No. | Structure |
| --- | --- |
| 36 | 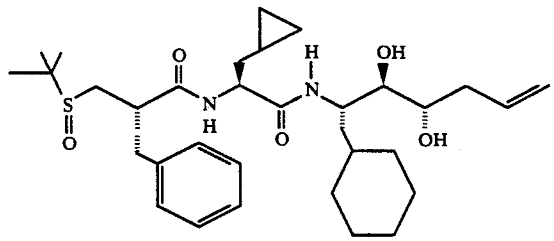 |

BIOLOGICAL EVALUATION

Human Renin Inhibition in vitro

Compounds of Formula I were evaluated as inhibitors of human renin in an in vitro assay, as follows: This human renin inhibition test has been previously described in detail [Papaioannou et al., *Clinical and Experimental Hypertension*, A7(9), 1243-1257 (1985)]. Human renin was obtained from the National Institute for Biological Standards, London. An incubation mixture was prepared containing the following components: in a total volume of 0.25 mL: 100 mM Tris-acetate buffer at pH 7.4, $25 \times 10^{-6}$ Goldblatt units of renin, 0.05 mL of plasma from human volunteers taking oral contraceptives, 6.0 mM Na-EDTA, 2.4 mM phenylmethyl sulfonyl fluoride, 1.5 mM 8-hydroxyquinoline, 0.4 mg/mL bovine serum albumin (BSA), and 0.024 mg/mL neomycin sulfate. This mixture was incubated for two hours at 37° C. in the presence or absence of renin inhibitors. The produced angiotensin I was determined by radioimmunoassay (New England Nuclear kit). Test compounds to be assayed were dissolved in DMSO and diluted with 100 mM Tris-acetate buffer at pH 7.4 containing 0.5% BSA to the appropriate concentration. The final concentration of organic solvent in the reaction mixture was less than 1%. Control incubations at 37° C. were used to correct for effects of organic solvent on renin activity. The in vitro enzymatic conversion of angiotensinogen to angiotensin I was inhibited by test compounds of the invention as indicated in Table II, below:

TABLE II

| Human Renin in vitro Inhibition Data | |
| --- | --- |
| Compound Example # | IC$_{50}$ Human Renin (nM) |
| Example 1 | 0.3 |
| Example 2 | 2.7 |

Also embraced within this invention is a class of pharmaceutical compositions comprising one or more compounds of Formula I in association with one or more non-toxic, pharmaceutically acceptable carriers and/or diluents and/or adjuvants (collectively referred to herein as "carrier" materials) and, if desired, other active ingredients. The compounds of the present invention may be administered by any suitable route, preferably in the form of a pharmaceutical composition adapted to such a route, and in a dose effective for the treatment intended. Therapeutically effective doses of the compounds of the present invention required to prevent or arrest the progress of the medical condition are readily ascertained by one of ordinary skill in the art. The compounds and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the active ingredient. Examples of such dosage units are tablets or capsules. These may with advantage contain an amount of active ingredient from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The active ingredient may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Compounds indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 400 mg of active compound per unit dosage form. A more preferred dosage will contain from about 2 mg to about 200 mg of active compound per unit dosage form. Most preferred is a dosage form containing from about 3 mg to about 100 mg of active compound per unit dose.

The dosage regimen for treating a disease condition with the compounds and/or compositions of this invention is selected in accordance with a variety of factors, including the type, age, weight, sex and medical condition of the patient, the severity of the disease, the route of administration, and the particular compound employed, and thus may vary widely.

For therapeutic purposes, the compounds of this invention are ordinarily combined with one or more adjuvants appropriate to the indicated route of administration. If administered per os, the compounds may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone,

What is claimed is:

1. A compound of Formula I:

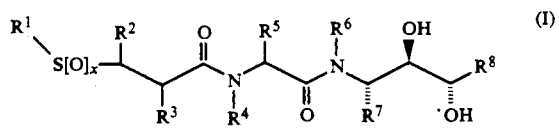

wherein $R^1$ is selected from the group consisting of alkyl, trifluoromethyl, cycloalkyl, cycloalkylalkyl, aryl, haloaryl, aralkyl and haloaralkyl; wherein x is a number selected from the group consisting of zero, one and two; wherein $R^2$ is selected from the group consisting of hydrido and alkyl; wherein $R^3$ is selected from the group consisting of hydrido, cycloalkylalkyl, aralkyl and haloaralkyl; wherein each of $R^4$ and $R^6$ is independently selected from the group consisting of hydrido and methyl; wherein $R^5$ is cyclopropylmethyl; wherein $R^7$ is selected from the group consisting of alkyl, cycloalkylalkyl and aralkyl; wherein $R^8$ is selected from the group consisting of hydrido, alkyl, hydroxyalkyl, cycloalkyl, cycloalkylalkyl, alkenyl and haloalkenyl; and wherein any one of said $R^1$ through $R^8$ groups having a substitutable position may be substituted with one or more groups selected from the group consisting of alkyl, hydroxy, alkoxy and alkenyl.

2. Compound of claim 1 wherein $R^1$ is selected from the group consisting of alkyl, trifluoromethyl, cycloalkyl, cycloalkylalkyl, phenyl, halophenyl, phenylalkyl, halophenylalkyl, naphthyl, halonaphthyl, naphthylaklyl and halonaphthylalkyl; wherein x is a number selected from the group consisting of zero, one and two; wherein $R^2$ is selected from the group consisting of hydrido and alkyl; wherein $R^3$ is selected from the group consisting of hydrido, cycloalkylalkyl, phenylalkyl, halophenylalkyl, naphthylalkyl and halonaphthylalkyl; wherein each of $R^4$ and $R^6$ is independently selected from the group consisting of hydrido and methyl; wherein $R^5$ is cyclopropylmethyl; wherein $R^7$ is selected from the group consisting of cyclohexylmethyl and benzyl, either one of which may be substituted with one or more groups selected from the group consisting of alkyl, hydroxy and alkoxy; and wherein $R^8$ is selected from the group consisting of hydrido, alkyl, cycloalkyl, cycloalkylalkyl, hydroxyalkyl, alkenyl and haloalkenyl.

3. Compound of claim 2 wherein $R^1$ is selected from the group consisting of methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from zero, one and two; wherein $R^2$ is selected from the group consisting of hydrido, methyl, ethyl and n-propyl; wherein $R^3$ is selected from the group consisting of hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from the group consisting of hydrido and methyl; wherein $R^5$ is cyclopropylmethyl; wherein $R^7$ is cyclohexylmethyl; and wherein $R^8$ is selected from the group consisting of methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

4. Compound of claim 3 wherein $R^1$ is selected from the group consisting of methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein $R^2$ is selected from the group consisting of hydrido, methyl, ethyl and n-propyl; wherein $R^3$ is selected from the group consisting of hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein $R^5$ is cyclopropylmethyl; wherein $R^7$ is cyclohexylmethyl; and wherein $R^8$ is selected from the group consisting of ethyl, n-propyl, n-butyl, isobutyl, cyclopropyl, cyclobutyl, cyclopropylmethyl, allyl and vinyl.

5. Compound of claim 4 wherein $R^1$ is selected from the group consisting of isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein x is zero or two; wherein $R^2$ is selected from the group consisting of hydrido, methyl, ethyl and phenyl; wherein $R^3$ is selected from the group consisting of hydrido, cyclohexylmethyl, benzyl, fluorobenzyl, chlorobenzyl, fluoronaphthylmethyl and chloronaphthylmethyl; wherein each of $R^4$ and $R^6$ is hydrido; wherein $R^5$ is cyclopropylmethyl; wherein $R^7$ is cyclohexylmethyl; and wherein $R^8$ is selected from the group consisting of n-propyl, isobutyl, cyclopropyl, cyclopropylmethyl, allyl and vinyl.

6. Compound of claim 5 selected from compounds, their tautomers, and the pharmaceutically-acceptable esters thereof, of the group consisting of

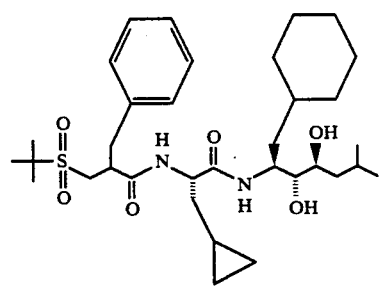
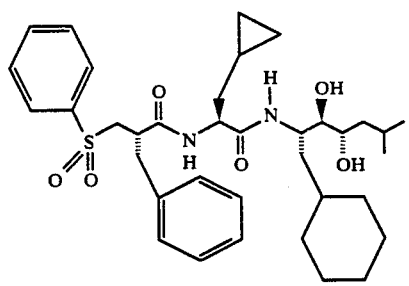
-continued
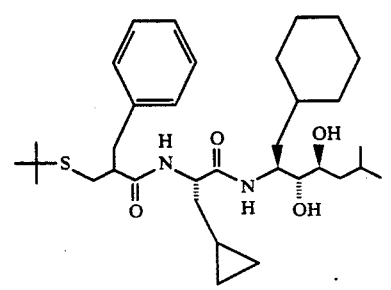
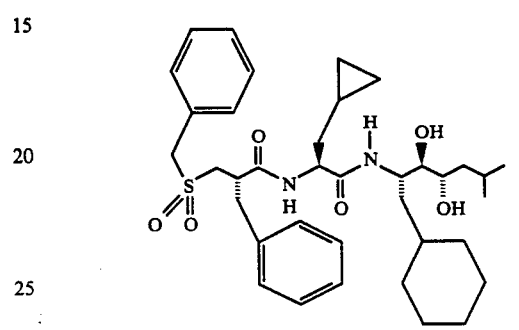
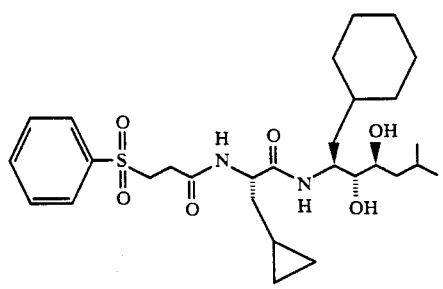
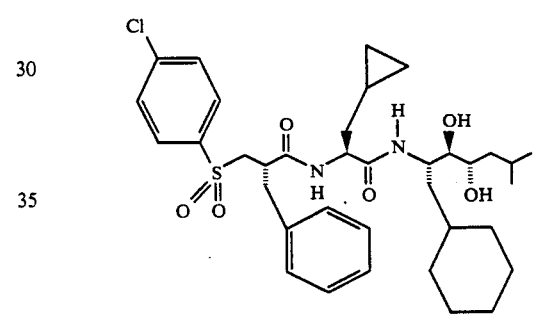
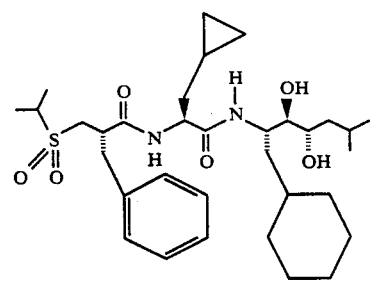
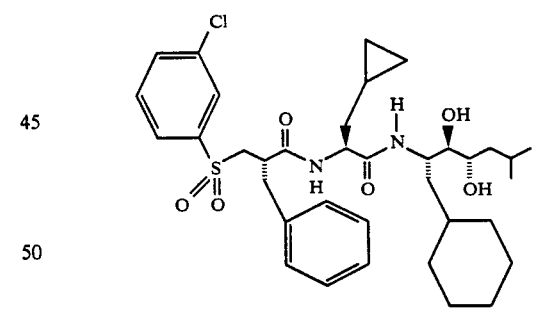
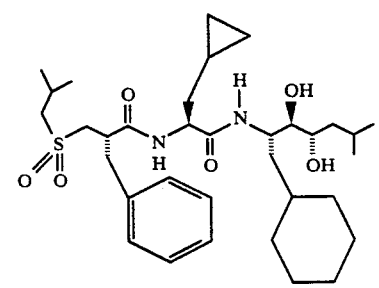
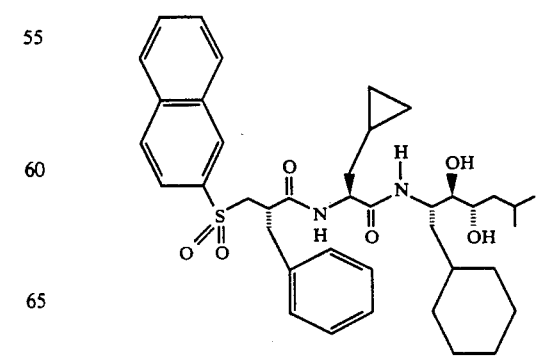

-continued

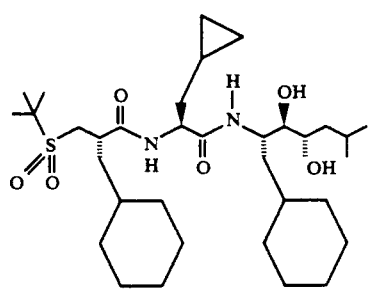

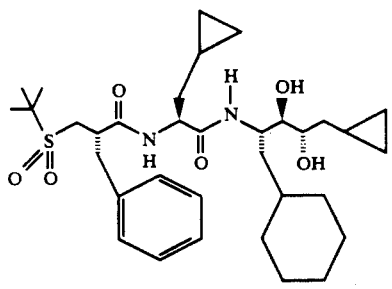

and

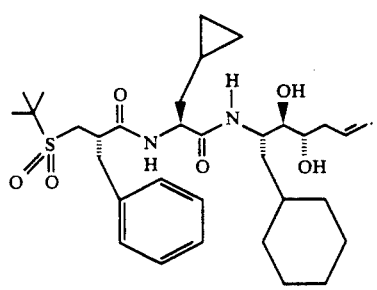

7. Compound of claim 6 which is N-[2-[[1S, 1R*-(cyclohexylmethyl)-2S*,3R*-dihydroxy-5-methylhexyl]amino]-1R*-(cyclopropylmethyl)-2-oxoethyl]-a-[[(1,1-dimethylethyl)sulfonyl]methyl]benzenepropanamide.

8. Compound of claim 6 which is N-[2-[[1S,1R*-(cyclohexylmethyl)-2S*,3R*-dihydroxy-5-methylhexyl]amino]-1R*-(cyclopropylmethyl)-2-oxoethyl]-a-[[(1,1-dimethylethyl)thio]methyl]benzenepropanamide.

9. Compound of claim 6 which is N-[[1S,1R*-(cyclohexylmethyl)-2S*,3R*-dihydroxy-5-methylhexyl]-aR*-[[1-oxo-3-(phenylsulfonyl)propyl]amino]cyclopropanepropanamide.

10. A pharmaceutical composition comprising a therapeutically-effective amount of a renin-inhibiting compound and a pharmaceutically-acceptable carrier or diluent, said renin-inhibiting compound selected from a family of compounds of Formula I:

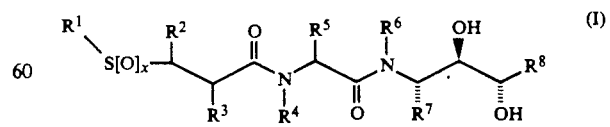

wherein $R^1$ is selected from the group consisting of alkyl, trifluoromethyl, cycloalkyl, cycloalkylalkyl, aryl, haloaryl, aralkyl and haloaralkyl; wherein x is a number selected from the group consisting of zero, one and two; wherein $R^2$ is selected from the group consisting of hydrido and alkyl; wherein R³ is selected from the group consisting of hydrido, cycloalkylalkyl, aralkyl and haloaralkyl; wherein each of R⁴ and R⁶ is independently selected from the group consisting of hydrido and methyl; wherein R⁵ is cyclopropylmethyl; wherein R⁷ is selected from the group consisting of alkyl, cycloalkylalkyl and aralkyl; wherein R⁸ is selected from the group consisting of hydrido, alkyl, hydroxyalkyl, cycloalkyl, cycloalkylalkyl, alkenyl and haloalkenyl; and wherein any one of said R¹ through R⁸ groups having a substitutable position may be substituted with one or more groups selected from the group consisting of alkyl, hydroxy, alkoxy and alkenyl.

11. The composition of claim 10 wherein R¹ is selected from the group consisting of alkyl, trifluoromethyl, cycloalkyl, cycloalkylalkyl, phenyl, halophenyl, phenylalkyl, halophenylalkyl, naphthyl, halonaphthyl, naphthylaklyl and halonaphthylalkyl; wherein x is a number selected from the group consisting of zero, one and two; wherein R² is selected from the group consisting of hydrido and alkyl; wherein R³ is selected from the group consisting of hydrido, cycloalkylalkyl, phenylalkyl, halophenylalkyl, naphthylalkyl and halonaphthylalkyl; wherein each of R⁴ and R⁶ is independently selected from the group consisting of hydrido and methyl; wherein R⁵ is cyclopropylmethyl; wherein R⁷ is selected from the group consisting of cyclohexylmethyl and benzyl, either one of which may be substituted with one or more groups selected from the group consisting of alkyl, hydroxy and alkoxy; and wherein R⁸ is selected from the group consisting of hydrido, alkyl, cycloalkyl, cycloalkylalkyl, hydroxyalkyl, alkenyl and haloalkenyl.

12. The composition of claim 11 wherein R¹ is selected from the group consisting of methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from the group consisting of zero, one and two; wherein R² is selected from the group consisting of hydrido, methyl, ethyl and n-propyl; wherein R³ is selected from the group consisting of hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is independently selected from the group consisting of hydrido and methyl; wherein R⁵ is cyclopropylmethyl; wherein R⁷ is cyclohexylmethyl; and wherein R⁸ is selected from the group consisting of methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

13. The composition of claim 12 wherein R¹ is selected from the group consisting of methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein R² is selected from the group consisting of hydrido, methyl, ethyl and n-propyl; wherein R³ is selected from the group consisting of hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of R⁴ and R⁶ is hydrido; wherein R⁵ is cyclopropylmethyl; wherein R⁷ is cyclohexylmethyl; and wherein R⁸ is selected from the group consisting of ethyl, n-propyl, n-butyl, isobutyl, cyclopropyl, cyclobutyl, cyclopropylmethyl, allyl and vinyl.

14. The composition of claim 13 wherein R¹ is selected from the group consisting of isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein R² is selected from the group consisting of hydrido, methyl, ethyl and phenyl; wherein R³ is selected from the group consisting of hydrido, cyclohexylmethyl, benzyl, fluorobenzyl, chlorobenzyl, fluoronaphthylmethyl and chloronaphthylmethyl; wherein each of R⁴ and R⁶ is hydrido; wherein R⁵ is cyclopropylmethyl; wherein R⁷ is cyclohexylmethyl; and wherein R⁸ is selected from the group consisting of n-propyl, isobutyl, cyclopropyl, cyclopropylmethyl allyl and vinyl.

15. The composition of claim 14 wherein said renin-inhibiting compound is N-[2-[[1S,1R*-(cyclohexylmethyl)-2S*,3R*-dihydroxy-5-methylhexyl]amino]-1R*-(cyclopropylmethyl)-2-oxoethyl]-α-[[(1,1-dimethylethyl)sulfonyl]methyl]benzenepropanamide.

16. The composition of claim 14 wherein said renin-inhibiting compound is N-[2-[[1S,1R*-(cyclohexylmethyl)-2S*,3R*-dihydroxy-5-methylhexyl]amino]-1R*-(cyclopropylmethyl)-2-oxoethyl]-α-[[(1,1-dimethylethyl)thio]methyl]benzenepropanamide.

17. The composition of claim 14 wherein said renin-inhibiting compound is N-[[1S,1R*-(cyclohexylmethyl)-2S*,3R*-dihydroxy-5-methylhexyl]-αR*-[[1-oxo-3-(phenylsulfonyl)propyl]amino]cyclopropanepropanamide.

18. A therapeutic method for treating hypertension, said method comprising administering to a hypertensive patient a therapeutically-effective amount of a compound of Formula I:

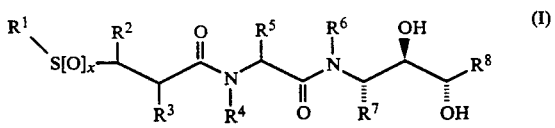

wherein R¹ is selected from the group consisting of alkyl, trifluoromethyl, cycloalkyl, cycloalkylalkyl, aryl, haloaryl, aralkyl and haloaralkyl; wherein x is a number selected from the group consisting of zero, one and two; wherein R² is selected from hydrido and alkyl; wherein R³ is selected from the group consisting of hydrido, cycloalkylalkyl, aralkyl and haloaralkyl; wherein each of R⁴ and R⁶ is independently selected from the group consisting of hydrido and methyl; wherein R⁵ is cyclopropylmethyl; wherein R⁷ is selected from the group consisting of alkyl, cycloalkylalkyl and aralkyl; wherein R⁸ is selected from the group consisting of hydrido, alkyl, hydroxyalkyl, cycloalkyl, cycloalkylalkyl, alkenyl and haloalkenyl; and wherein any one of said R¹ through R⁸ groups having a substitutable position may be substituted with one or more groups selected from the group consisting of alkyl, hydroxy, alkoxy and alkenyl.

19. The method of claim 18 wherein $R^1$ is selected from the group consisting of alkyl, trifluoromethyl, cycloalkyl, cycloalkylalkyl, phenyl, halophenyl, phenylalkyl, halophenylalkyl, naphthyl, halonaphthyl, naphthylaklyl and halonaphthylalkyl; wherein x is a number selected from the group consisting of zero, one and two; wherein $R^2$ is selected from the group consisting of hydrido and alkyl; wherein $R^3$ is selected from the group consisting of hydrido, cycloalkylalkyl, phenylalkyl, halophenylalkyl, naphthylalkyl and halonaphthylalkyl; wherein each of $R^4$ and $R^6$ is independently selected from the group consisting of hydrido and methyl; wherein $R^5$ is cyclopropylmethyl; wherein $R^7$ is selected from the group consisting of cyclohexylmethyl and benzyl, either one of which may be substituted with one or more groups selected from alkyl, hydroxy and alkoxy; and wherein $R^8$ is selected from the group consisting of hydrido, alkyl, cycloalkyl, cycloalkylalkyl, hydroxyalkyl, alkenyl and haloalkenyl.

20. The method of claim 19 wherein $R^1$ is selected from the group consisting of methyl, ethyl, n-propyl, isopropyl, n-butyl, isobutyl, sec-butyl, tert-butyl, trifluoromethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is a number selected from the group consisting of zero, one and two; wherein $R^2$ is selected from the group consisting of hydrido, methyl, ethyl and n-propyl; wherein $R^3$ is selected from the group consisting of hydrido, cyclohexylmethyl, benzyl, phenylethyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is independently selected from the group consisting of hydrido and methyl; wherein $R^5$ is cyclopropylmethyl; wherein $R^7$ is cyclohexylmethyl; and wherein $R^8$ is selected from the group consisting of methyl, ethyl, n-propyl, isopropyl, n-butyl, isobutyl, sec-butyl, tert-butyl, cyclopropyl, cyclobutyl, cyclopropylmethyl, cyclobutylmethyl, cyclohexylmethyl, allyl and vinyl.

21. The method of claim 20 wherein $R^1$ is selected from the group consisting of methyl, ethyl, n-propyl, isopropyl, benzyl, phenethyl, phenyl, fluorophenyl, chlorophenyl, trifluoromethylphenyl, benzyl, phenylethyl, phenylpropyl, fluorobenzyl, fluorophenylethyl, fluorophenylpropyl, chlorobenzyl, chlorophenylethyl, chlorophenylpropyl, naphthyl, fluoronaphthyl, chloronaphthyl, naphthylmethyl, naphthylethyl, fluoronaphthylmethyl and chloronaphthylmethyl; wherein x is zero or two; wherein $R^2$ is selected from the group consisting of hydrido, methyl, ethyl and n-propyl; wherein $R^3$ is selected from the group consisting of hydrido, cyclohexylmethyl, benzyl, phenylethyl, phenylpropyl, fluorobenzyl, fluorophenylethyl, chlorobenzyl, chlorophenylethyl, naphthylmethyl, naphthylethyl, fluoronaphthylmethyl and chloronaphthylmethyl; wherein each of $R^4$ and $R^6$ is hydrido; wherein $R^5$ is cyclopropylmethyl; wherein $R^7$ is cyclohexylmethyl; and wherein $R^8$ is selected from the group consisting of ethyl, n-propyl, n-butyl, isobutyl, cyclopropyl, cyclobutyl, cyclopropylmethyl, allyl and vinyl.

22. The method of claim 21 wherein $R^1$ is selected from the group consisting of isopropyl, isobutyl, sec-butyl, tert-butyl, phenyl, fluorophenyl, chlorophenyl, benzyl, fluorobenzyl, chlorobenzyl, naphthyl, fluoronaphthyl, chloronaphthyl, fluoronaphthylmethyl and chloronaphthylmethyl; wherein $R^2$ is selected from the group consisting of hydrido, methyl, ethyl and phenyl; wherein $R^3$ is selected from the group consisting of hydrido, cyclohexylmethyl, benzyl, fluorobenzyl, chlorobenzyl, fluoronaphthylmethyl and chloronaphthylmethyl; wherein each of $R^4$ and $R^6$ is hydrido; wherein $R^5$ is cyclopropylmethyl; wherein $R^7$ is cyclohexylmethyl; and wherein $R^8$ is selected from the group consisting of n-propyl, isobutyl, cyclopropyl, cyclopropylmethyl, allyl and vinyl.

23. The method of claim 22 wherein said compound is N-[2-[[1S,1R*-(cyclohexylmethyl)-2S*,3R*-dihydroxy-5-methylhexyl]amino]-1R*-(cyclopropylmethyl)-2-oxoethyl]-α-[[(1,1-dimethylethyl)sulfonyl]methyl]benzenepropanamide.

24. The method of claim 22 wherein said compound is N-[2-[[1S,1R*-(cyclohexylmethyl)-2S*,3R*-dihydroxy-5-methylhexyl]amino]-1R*-(cyclopropylmethyl)-2-oxoethyl]-α-[[(1,1-dimethylethyl)thio]methyl]benzenepropanamide.

25. The method of claim 22 wherein said compound is N-[[1S,1R*-(cyclohexylmethyl)-2S*,3R*-dihydroxy-5-methylhexyl]-αR*-[[1-oxo-3-(phenylsulfonyl)propyl]amino]cyclopropanepropanamide.

* * * * *